United States Patent [19]
Swanson et al.

[11] Patent Number: 5,836,874
[45] Date of Patent: Nov. 17, 1998

[54] MULTI-FUNCTION ELECTRODE STRUCTURES FOR ELECTRICALLY ANALYZING AND HEATING BODY TISSUE

[75] Inventors: David K. Swanson, Mountain View; Dorin Panescu, Sunnyvale; James G. Whayne, Saratoga; Jerome Jackson, Sunnyvale, all of Calif.

[73] Assignee: EP Technologies, Inc., Sunnyvale, Calif.

[21] Appl. No.: 629,014

[22] Filed: Apr. 8, 1996

Related U.S. Application Data

[60] Provisional application No. 60/010,223, Jan. 19, 1996, provisional application No. 60/010,225, Jan. 19, 1996 and provisional application NO. 60/010,354, Jan. 19, 1996.

[51] Int. Cl.⁶ .............................. A61B 5/04; A61B 17/39
[52] U.S. Cl. ............................. 600/374; 606/41; 607/99; 607/122
[58] Field of Search .................................. 606/41, 45, 33; 600/374; 607/99, 105, 113, 122

[56] References Cited

U.S. PATENT DOCUMENTS

| | | |
|---|---|---|
| 4,979,948 | 12/1990 | Geddes et al. . |
| 5,195,969 | 3/1993 | Wang et al. . |
| 5,255,678 | 10/1993 | Deslauriers et al. . |
| 5,277,201 | 1/1994 | Stern . |
| 5,293,869 | 3/1994 | Edwards et al. . |
| 5,311,866 | 5/1994 | Kagan et al. . |
| 5,334,193 | 8/1994 | Nardella . |
| 5,391,200 | 2/1995 | Kenknight et al. . |
| 5,462,545 | 10/1995 | Wang et al. . |
| 5,472,441 | 12/1995 | Edwards et al. . |
| 5,505,730 | 4/1996 | Edwards . |
| 5,562,720 | 10/1996 | Stern et al. . |
| 5,569,241 | 10/1996 | Edwards . |
| 5,598,848 | 2/1997 | Swanson et al. . |

FOREIGN PATENT DOCUMENTS

| | | |
|---|---|---|
| 0 080 536A | 6/1983 | European Pat. Off. . |
| 3516830 | 11/1986 | Germany . |
| 1220-673A | 3/1986 | Russian Federation . |
| WO95/01751 | 1/1995 | WIPO . |
| WO 96/00041 | 1/1996 | WIPO . |

OTHER PUBLICATIONS

Fann et al., Endocardial Activation Mapping and Endocardial Pace–Mapping Using a Balloon Apparatus, The American Journal of Cardiology, Apr. 1, 1995, pp. 1076–1083.

*Primary Examiner*—Lee S. Cohen
*Attorney, Agent, or Firm*—Lyon & Lyon LLP

[57] ABSTRACT

Systems and methods for heating body tissue place a multi-function structure having an exterior wall in contact with body tissue. The structure includes an array of electrically conducting electrode segments carried by the exterior wall. An electrically conductive network is coupled to the electrode segments, including at least one electrically conductive path individually coupled to each electrode segment. The systems and methods operate in a first mode during which the network is electrically conditioned to individually sense at each electrode segment local electrical events in tissue, such as electrical potentials, resistivity, or impedance. The systems and methods operate in a second mode during which the network is electrically conditioned, based at least in part upon local electrical events sensed by the electrode segments, to couple at least two electrode segments together to simultaneously transmit electrical energy to heat or ablate a region of body tissue.

84 Claims, 7 Drawing Sheets

Fig. 9

MULTI-FUNCTION ELECTRODE STRUCTURES FOR ELECTRICALLY ANALYZING AND HEATING BODY TISSUE

This application claims the benefit of U.S. Provisional Applications having Ser. Nos. 60/010,223, 60/010,225 and 60/010,354, all of which were filed on Jan. 19, 1996. Applicants hereby request that priority to these three provisional applications be claimed pursuant to 35 U.S.C. § 119(e) and not 35 U.S.C. § 120 as identified in the declaration for this application.

FIELD OF THE INVENTION

The invention generally relates to electrode structures deployed in interior regions of the body. In a more specific sense, the invention relates to electrode structures deployable into the heart for diagnosis and treatment of cardiac conditions.

BACKGROUND OF THE INVENTION

Physicians examine the propagation of electrical impulses in heart tissue to locate aberrant conductive pathways. The aberrant conductive pathways constitute peculiar and life threatening patterns, called dysrhythmias. The techniques used to analyze these pathways, commonly called "mapping," identify regions in the heart tissue, called foci, which are ablated to treat the dysrhythmia.

Conventional cardiac tissue mapping techniques use multiple electrodes positioned in contact with epicardial heart tissue to obtain multiple electrograms. Digital signal processing algorithms convert the electrogram morphologies into isochronal displays, which depict the propagation of electrical impulses in heart tissue over time. These conventional mapping techniques require invasive open heart surgical techniques to position the electrodes on the epicardial surface of the heart.

Furthermore, conventional epicardial electrogram processing techniques used for detecting local electrical events in heart tissue are often unable to interpret electrograms with multiple morphologies. Such electrograms are encountered, for example, when mapping a heart undergoing ventricular tachycardia (VT). For this and other reasons, consistently high correct foci identification rates (CIR) cannot be achieved with current multi-electrode mapping technologies.

Researchers have taken epicardial measurements of the electrical resistivity of heart tissue. Their research indicates that the electrical resistivity of infarcted heart tissue is about one-half that of healthy heart tissue. Their research also indicates that ischemic tissue occupying the border zone between infarcted tissue and healthy tissue has an electrical resistivity that is about two-thirds that of healthy heart tissue. See, e.g., Fallert et al., "Myocardial Electrical Impedance Mapping of Ischemic Sheep Hearts and Healing Aneurysms," Circulation, Vol. 87, No. 1, January 1993, 199–207.

Panescu U.S. Pat. No. 5,487,391 and Panescu et al U.S. Pat. No. 5,485,849 demonstrate that this observed physiological phenomenon, when coupled with effective, non-intrusive measurement techniques, can lead to cardiac mapping systems and procedures with a CIR better than conventional mapping technologies. The Panescu '391 and '849 Patents use a multiple electrode structure and signal processing methodologies to examine heart tissue morphology quickly, accurately, and in a relatively non-invasive manner. The systems and methods disclosed in the Panescu '391 and '849 Patents transmit electrical current through a region of heart tissue lying between selected pairs of the electrodes, at least one of the electrodes in each pair being located within the heart. Based upon these current transmissions, the systems and methods derive the electrical characteristic of tissue lying between the electrode pairs. This electrical characteristic (called the "E-Characteristic") can be directly correlated to tissue morphology. A low relative E-Characteristic indicates infarcted heart tissue, while a high relative E-Characteristic indicates healthy heart tissue. Intermediate E-Characteristic values indicate the border of ischemic tissue between infarcted and healthy tissue.

The treatment of cardiac arrhythmias also requires electrodes capable of creating tissue lesions having a diversity of different geometries and characteristics, depending upon the particular physiology of the arrhythmia to be treated.

For example, a conventional 8F diameter/4 mm long cardiac ablation electrode can transmit radio frequency energy to create lesions in myocardial tissue with a depth of about 0.5 cm and a width of about 10 mm, with a lesion volume of up to 0.2 cm$^3$. These small and shallow lesions are desired in the sinus node for sinus node modifications, or along the A-V groove for various accessory pathway ablations, or along the slow zone of the tricuspid isthmus for atrial flutter (AFL) or AV node slow pathways ablations.

However, the elimination of ventricular tachycardia (VT) substrates is thought to require significantly larger and deeper lesions, with a penetration depth greater than 1.5 cm, a width of more than 2.0 cm, with a lesion volume of at least 1 cm$^3$.

There also remains the need to create lesions having relatively large surface areas with shallow depths.

One proposed solution to the creation of diverse lesion characteristics is to use different forms of ablation energy. However, technologies surrounding microwave, laser, ultrasound, and chemical ablation are largely unproven for this purpose.

The use of active cooling in association with the transmission of DC or radio frequency ablation energy is known to force the electrode-tissue interface to lower temperature values, As a result, the hottest tissue temperature region is shifted deeper into the tissue, which, in turn, shifts the boundary of the tissue rendered nonviable by ablation deeper into the tissue. An electrode that is actively cooled can be used to transmit more ablation energy into the tissue, compared to the same electrode that is not actively cooled. However, control of active cooling is required to keep maximum tissue temperatures safely below about 100° C., at which tissue desiccation or tissue boiling is known to occur.

Another proposed solution to the creation of larger lesions, either in surface area and/or depth, is the use of substantially larger electrodes than commercially available. Yet, larger electrodes themselves pose problems of size and maneuverability, which weigh against a safe and easy introduction of large electrodes through a vein or artery into the heart.

A need exists for multi-purpose cardiac ablation electrodes that can both examine the propagation of electrical impulses in heart tissue and also create lesions of different geometries and characteristics. Multi-purpose electrodes would possess the requisite flexibility and maneuverability permitting safe and easy introduction into the heart. Once deployed inside the heart, these electrodes would possess the capability to map cardiac tissue and to emit energy sufficient to create, in a controlled fashion, either large and deep lesions, or small and shallow lesions, or large and shallow lesions, depending upon the therapy required.

SUMMARY OF THE INVENTION

One aspect of the invention provides multi-function systems and methods for use in association with body tissue. The systems and methods employ a structure including an exterior wall adapted to contact tissue, which carries an array of electrically conducting electrode segments. An electrically conductive network is coupled to the electrode segments, including at least one electrically conductive path individually coupled to each electrode segment. A controller is coupled to the electrically conductive network. The controller operates in a first mode during which the network is electrically conditioned to individually sense at each electrode segment local electrical events in tissue, such as electrical potentials, resistivity, or impedance. The controller further operates in a second mode during which the network is electrically conditioned, based at least in part upon local electrical events sensed by the electrode segments, to couple at least two electrode segments together to simultaneously transmit electrical energy to create a physiological effect upon a region of body tissue, such as heating or ablating the tissue region.

According to another aspect of the invention, the controller operates in conjunction with the array of electrode segments in a first mode during which the network is electrically conditioned to individually transmit through each electrode segment electrical energy creating a local physiological effect upon body tissue, such as electrically stimulating localized tissue. The controller further operates in a second mode during which the network is electrically conditioned to couple at least two electrode segments together to simultaneously transmit electrical energy creating a regional physiological effect upon body tissue, such as heating or ablating the tissue region.

Another aspect of the invention provides systems and methods for pacing heart tissue. The systems and methods make use of a structure including an exterior wall adapted to contact heart tissue. The exterior wall is adapted to selectively assume an expanded geometry having a first maximum diameter and a collapsed geometry having a second maximum diameter less than the first maximum diameter. The exterior wall carries electrically conducting electrodes. An electrically conductive network is coupled to the electrodes, including at least one electrically conductive path individually coupled to each electrode. According to this aspect of the invention, a controller is coupled to the electrically conductive network. The controller operates in a first mode during which the network is electrically conditioned to transmit electrical energy through the electrodes to pace heart tissue. The controller further operates in a second mode during which the network is electrically conditioned to sense electrical events through the electrodes.

Other features and advantages of the inventions are set forth in the following Description and Drawings, as well as in the appended claims.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
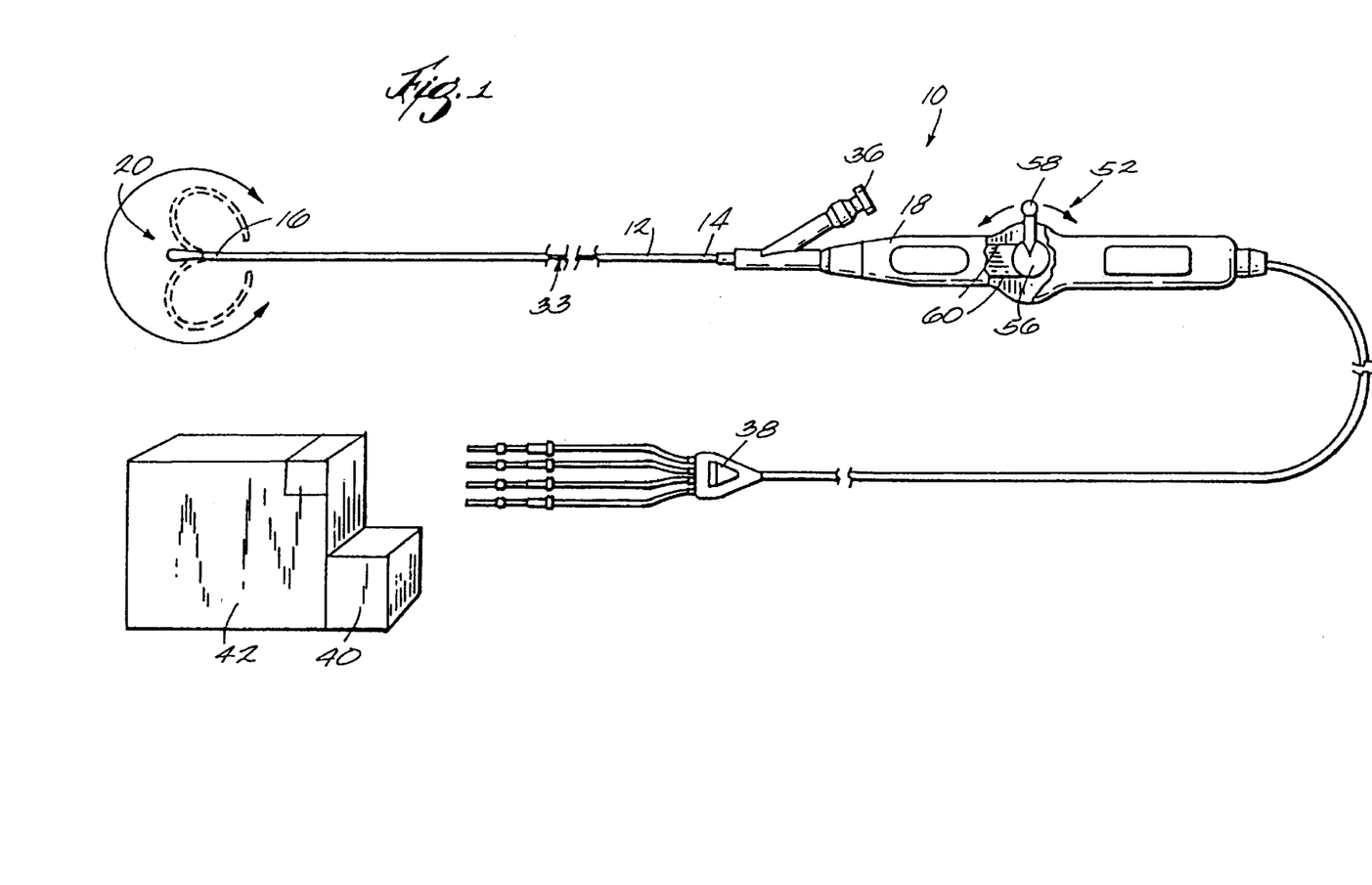
FIG. 1 is a view of a system for analyzing the morphology of heart tissue that embodies the features of the invention.

FIG. 1 shows the components of a system 10 for examining heart tissue morphology.

The system 10 includes a flexible catheter tube 12 with a proximal end 14 and a distal end 16. The proximal end 14 carries a handle 18. The distal end 16 carries an electrode structure 20, which embodies features of the invention.

The physician uses the electrode structure 20 in association with a process controller 40 to take multiple, sequential measurements of the transmission of electrical current through heart tissue. Based upon these current transmissions, the controller 40 derives the electrical characteristic of tissue lying between the electrode pairs, called the "E-Characteristic". The E-Characteristic can be directly correlated to tissue morphology.

The electrode structure 20 can be also used to ablate tissue in the system 10.

Figure 2:
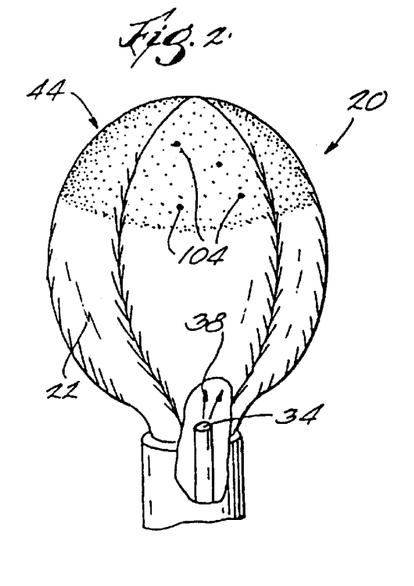
FIG. 2 is an enlarged side view of an expandable-collapsible electrode structure associated with the system shown in FIG. 1, shown in the expanded geometry.
Figure 3:
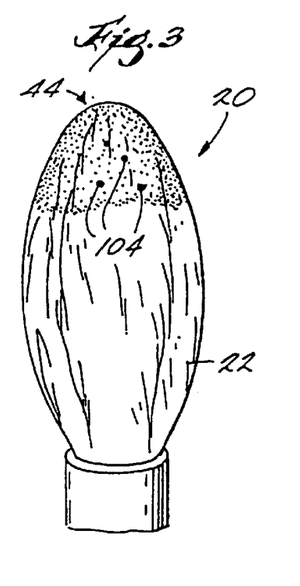
FIG. 3 is an enlarged side view of the expandable-collapsible electrode structure shown in FIG. 2, shown in the collapsed geometry.

As FIGS. 2 and 3 best show, the electrode structure 20 includes an expandable-collapsible body 22. The geometry of the body 22 can be altered between a collapsed geometry (FIG. 3) and an enlarged, or expanded, geometry (FIG. 2). In the illustrated and preferred embodiment, fluid pressure is used to inflate and maintain the expandable-collapsible body 22 in the expanded geometry.

In this arrangement (see FIG. 2), the catheter tube 12 carries an interior lumen 34 along its length. The distal end of the lumen 34 opens into the hollow interior of the expandable-collapsible body 22. The proximal end of the lumen 34 communicates with a port 36 (see FIG. 1) on the handle 18. The fluid inflation medium (arrows 38 in FIG. 2) is conveyed under positive pressure through the port 36 and into the lumen 34. The fluid medium 38 fills the interior of the expandable-collapsible body 22. The fluid medium 38 exerts interior pressure to urge the expandable-collapsible body 22 from its collapsed geometry to the enlarged geometry.

This characteristic allows the expandable-collapsible body 22 to assume a collapsed, low profile (ideally, less than 8 French diameter, i.e., less than about 0.267 cm) when introduced into the vasculature. Once located in the desired position, the expandable-collapsible body 22 can be urged into a significantly expanded geometry of, for example, approximately 7 to 20 mm.

Figure 5:
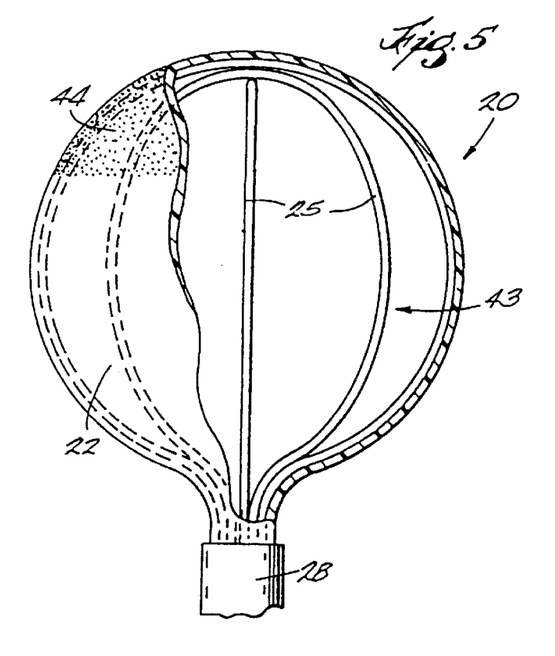
FIG. 5 is a side elevation view of an expandable-collapsible electrode structure associated with the system shown in FIG. 1, with an interior spline support structure shown in its expanded geometry.
Figure 6:
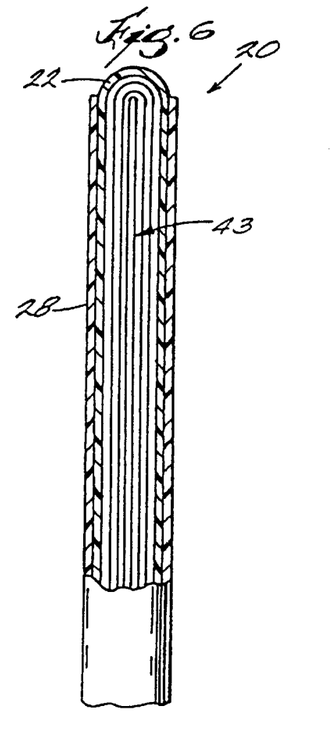
FIG. 6 is a side elevation view of the expandable-collapsible electrode structure shown in FIG. 5, with its interior spline support structure shown in its collapsed geometry.
Figure 7:
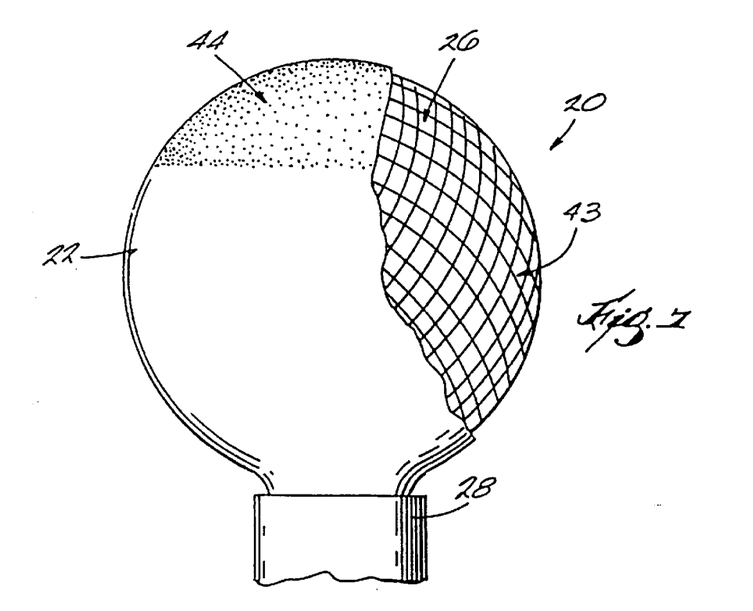
FIG. 7 is a side elevation view of an expandable-collapsible electrode structure associated with the system shown in FIG. 1, with an interior mesh support structure shown in its expanded geometry.

As FIGS. 5 to 7 show, the structure 20 can include, if desired, a normally open, yet collapsible, interior support structure 43 to apply internal force to augment or replace the force of fluid medium pressure to maintain the body 22 in the expanded geometry. The form of the interior support structure 43 can vary. It can, for example, comprise an assemblage of flexible spline elements 25, as shown in FIG. 5, or an interior porous, interwoven mesh or open cell foam structure 26, as shown in FIG. 7.

In these arrangements (see FIG. 6), the internally supported expandable-collapsible body 22 is brought to a collapsed geometry, after the removal of the inflation medium, by outside compression applied by an outer sheath 28 (see FIG. 6), which slides along the catheter tube 12. As FIG. 6 shows, forward movement of the sheath 28 advances it over the expanded expandable-collapsible body 22. The expandable-collapsible body 22 collapses into its low profile geometry within the sheath 28. Rearward movement of the sheath 28 (see FIGS. 5 or 7) retracts it away from the expandable-collapsible body 22. Free from the confines of the sheath 48, the interior support structure 43 springs open to return the expandable-collapsible body 22 to its expanded geometry to receive the fluid medium.

The expandable-collapsible body 22 can be formed about the exterior of a glass mold. In this arrangement, the external dimensions of the mold match the desired expanded geometry of the expandable-collapsible body 22. The mold is dipped in a desired sequence into a solution of the body material until the desired wall thickness is achieved. The mold is then etched away, leaving the formed expandable-collapsible body 22.

Alternatively, the expandable-collapsible body 22 may also be blow molded from extruded tube. In this arrangement, the body 22 is sealed at one end using adhesive or thermal fusion. The opposite open end of the body 22 is left open. The sealed expandable-collapsible body 22 is placed inside the mold. An inflation medium, such as high pressure gas or liquid, is introduced through the open tube end. The mold is exposed to heat as the tube body 22 is inflated to assume the mold geometry. The formed expandable-collapsible body 22 is then pulled from the mold.

Various specific geometries, of course, can be selected. The preferred geometry is essentially spherical and symmetric, with a distal spherical contour, as FIG. 2 shows. However, nonsymmetric or nonspherical contours can be used, depending upon the contour of the underlying tissue to be contacted during use. For example, when used in the ventricle, the body 22 should have a generally spherical contour. When used in the atrium, the body 22 should have a generally elongated contour. When used epicardially, the body 22 should have a generally concave contour.

Figure 4:
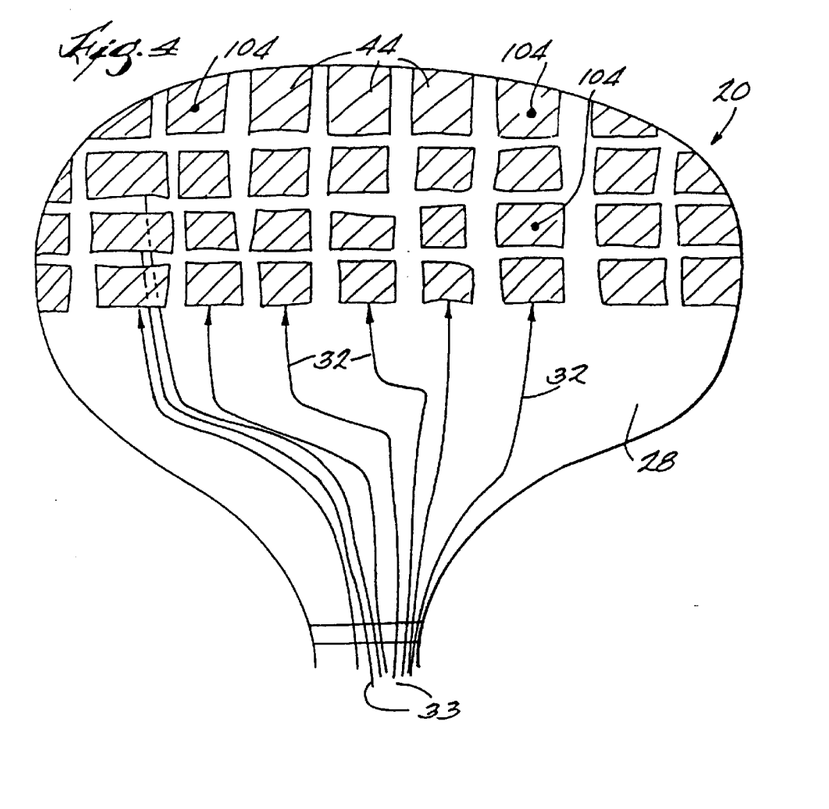
FIG. 4 is an enlarged and somewhat diagrammatic view of the surface of the electrode structure shown in FIGS. 2 and 3, showing the high density pattern of electrode segments.

As FIG. 4 best shows, the structure 20 includes an array of small electrode segments 44 overlying all or a portion of the expandable-collapsible body 22. The array orients the small electrode segments 44 in a high density, closely spaced relationship. The resistivity of each electrode segment 44 is low relative to the resistivity of the body 22 spacing the segments 44 apart.

The electrode segments 44 comprise metal, such as gold, platinum, platinum/iridium, among others, deposited upon the expandable-collapsible body 22 by sputtering, vapor deposition, ion beam deposition, electroplating over a deposited seed layer, photo-etching, multi-layer processes, or a combination of these processes.

A signal path 32 made from a highly conductive metal, like copper, leads from each electrode segment 44. The signal paths 32 are deposited on the body using conventional photo-etching or multi-layer processes. The signal paths 32 communicate with wires 33, which extend through catheter tube 12 for coupling to connectors 38 carried by the handle 18.

When deployed inside the heart chamber in its expanded geometry, the body 22 holds the array of electrodes segments 44 in intimate contact against the endocardial surface of the heart chamber. In the illustrated and preferred embodiment, a distal steering mechanism 52 (see FIG. 1) enhances the manipulation of the electrode structure 20 both during and after deployment. The steering mechanism 52 can vary. In the illustrated embodiment (see FIG. 1), the steering mechanism 52 includes a rotating cam wheel 56 coupled to an external steering lever 58 carried by the handle 18. The cam wheel 56 holds the proximal ends of right and left steering wires 60. The wires 60 pass with the signal wires 33 through the catheter tube 12 and connect to the left and right sides of a resilient bendable wire or leaf spring (not shown) adjacent the distal tube end 16. Further details of this and other types of steering mechanisms are shown in Lundquist and Thompson U.S. Pat. No. 5,254,088, which is incorporated into this Specification by reference. When deployed, the array of electrode segments 44 functions in both a diagnostic mode and a therapeutic mode.

In the diagnostic mode, each segment 44 is conditioned by the controller 40 to transmit electrical current through tissue. The electrode segments 44 can transmit electrical current in either a unipolar mode or a bipolar mode. When operated in a unipolar mode, the current return path is provided by an exterior indifferent electrode attached to the patient. When operated in a bipolar mode, the current return path is provided by an electrode segment located immediately next to or spaced away from the selected transmitting electrode segment 44.

From this, the controller 40 acquires impedance information about the heart tissue region that the electrode segments 44 contact. The impedance information is processed by the controller 40 to derive the E-Characteristic, which assists the physician in identifying regions of infarcted tissue where ablation therapy may be appropriate. The coupled electrode segments 44, being held by the body in intimate contact with tissue and thereby shielded from contact with the blood pool, direct essentially all current flow into tissue, thereby obtaining tissue characteristic information free of artifacts. The high density of electrode segments 44 carried by the expandable-collapsible body 22 also provides superior signal resolution for more accurate identification of the potential ablation region.

Further details of specific operation of the process controller 40 in deriving the E-Characteristics are disclosed in U.S. Pat. Nos. 5,485,849 and 5,487,391, which is incorporated herein by reference.

In the therapeutic mode, the controller 40 electrically couples a grid of adjacent electrode segments 44 together overlying the identified region to a source 42 of ablation energy. The coupled electrode segments simultaneously receive ablation energy from the source 42 (see FIG. 1), thereby serving as a large-surface area transmitter of the energy. While the type of ablation energy used can vary, in the illustrated and preferred embodiment, the coupled electrode segments 44 transmit radio frequency (RF) electromagnetic energy. The ablation energy from the coupled electrode segments pass through tissue, typically to an external patch. electrode (forming a unipolar arrangement). Alternatively, the transmitted energy can pass through tissue to a separate adjacent electrode in the heart chamber (forming a bipolar arrangement). The radio frequency energy heats the tissue, mostly ohmically, forming a lesion.

A controller 43 preferably governs the conveyance of radio frequency ablation energy from the generator 42 to the selected coupled electrode segments 44. In the preferred embodiment (see FIG. 2), the array of electrode segments 44 carries one or more temperature sensing elements 104, which are coupled to the controller 43. Temperatures sensed by the temperature sensing elements 104 are processed by the controller 43. Based upon temperature input, the controller 43 adjusts the time and power level of radio frequency energy transmissions by the coupled electrode segments 44, to achieve the desired lesion patterns and other ablation objectives. The temperature sensing elements 104 can take the form of thermistors, thermocouples, or the equivalent.

Various ways for attaching temperature sensing elements to an expandable-collapsible electrode body are described in copending patent application entitled "Expandable-Collapsible Electrode Structures" filed concurrently with this application.

Further details of the use of multiple ablation energy transmitters controlled using multiple temperature sensing elements are disclosed in copending U.S. patent application Ser. No. 08/286,930, filed Aug. 8, 1994, and entitled "Systems and Methods for Controlling Tissue Ablation Using Multiple Temperature Sensing Elements".

Figure 8:
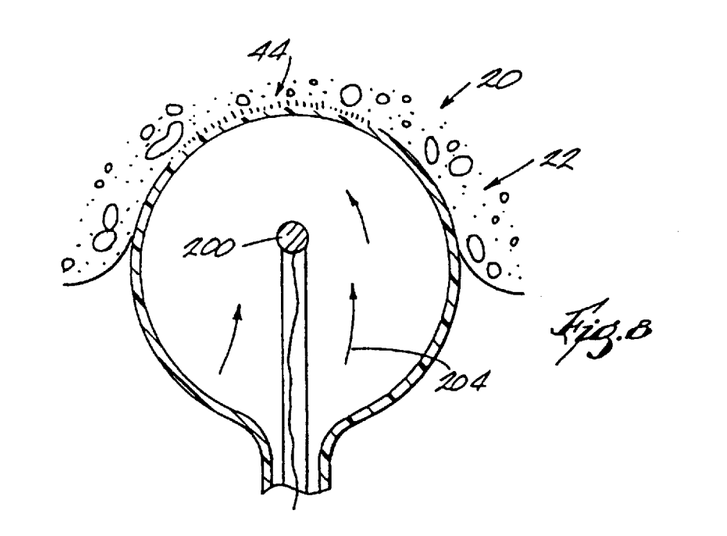
FIG. 8 is a side elevation view of an expandable-collapsible electrode structure associated with the system shown in FIG. 1, the structure having an electrically conductive body.

In an alternative embodiment (see FIG. 8), the body 22 can itself be electrically conductive, having a resistivity similar to the tissue it contacts (i.e., about 500 ohm·cm), or greater or more than this amount. The body can be made conductive by the inclusion by coextrusion of an electrically conductive material, like carbon black or chopped carbon fiber. In this arrangement, the electrically conductive body 22 is used in association with an interior electrode 200, like that shown in FIG. 8. In such an arrangement, a hypertonic saline solution 204 also fills the interior of the electrically conductive body 22 (as also shown in FIG. 8), to serve as an electrically conductive path to convey radio frequency energy from the electrode 200 to the body 22. In effect, in this arrangement, the electrically conductive body 22 functions as a "leaky" capacitor in transmitting radio frequency energy from the interior electrode 200 to tissue.

The amount of electrically conductive material coextruded into the body 22 affects the electrical conductivity, and thus the electrical resistivity of the body 22, which varies inversely with conductivity. Addition of more electrically conductive material increases electrical conductivity of the body 22, thereby reducing electrical resistivity of the body 22, and vice versa. The user selects a body 22 with a given resistivity according to a function that correlates desired lesion characteristics with the electrical resistivity values of the associated body 22. According to this function, resistivities equal to or greater that about 500 ohm·cm result in more shallow lesions, while resistivities less than about 500 ohm·cm result in deeper lesions, and vice versa.

Further details of electrode structures having electrically conductive bodies are disclosed in copending patent application entitled "Expandable-Collapsible Electrode Structures With Electrically Conductive Walls" (Attorney Docket 2458-A1), filed concurrently with this application.

Alternatively, the body 22 can be made electrically conductive by being made porous. Used in association with the interior electrode 200 and hypertonic solution 204 within the body 22, the pores of the porous body 22 establishes ionic transport of ablation energy from the electrode 200, through the electrically conductive medium 204, to tissue outside the body.

The electrode segments 44 can be used in tandem with the electrically conductive body to convey radio frequency energy to ablate tissue. At the same time the controller 40 electrically couples a grid of adjacent electrode segments 44 together to a source 42 of ablation energy, the interior electrode 200 also receives radio frequency energy for transmission by the medium 204 through the electrically conductive body 22. The conductive body 22 extends the effective surface area of the coupled segments 44, thereby enhancing the ablation effect.

If the body 22 is porous enough to actually perfuse liquid, an interior electrode 200 is not required to increase the effective electrode surface area of the segments 44. The perfusion of hypertonic liquid through the pores at the time the regions transmit radio frequency energy is itself sufficient to increase the effective transmission surface area of the segments 44. However, if the pores of porous body 22 are smaller, so that ionic transfer is not driven principally by perfusion, it is believed that it would be advantageous in increasing the effective surface area to also transmit radio frequency energy using an interior electrode 200 at the same time that radio frequency is being delivered to the segments 44 for transmission.

It should also be appreciated that, in this embodiment, the segments 44 can themselves be made from a porous, electrically conducting material. In this way, ionic transport can occur by mass transfer or perfusion through the segment 44 themselves.

Further details of a liquid filled porous electrode structure are disclosed in copending patent application entitled "Expandable-Collapsible Porous Electrode Structures" filed concurrently with this application.

The expandable-collapsible electrode structure 20 shown in FIG. 2 can also be used in association with conventional pacing apparatus (not shown) for pacing the heart to acquire electrograms in a conventional fashion. The pacing apparatus is electrically coupled to the connectors 38 to provide a pacing signal to a selected one electrode segment 44, generating depolarization foci at selected sites within the heart. The electrode segments 44 also serve to sense the resulting electrical events for the creation of electrograms. Used in this fashion, the structure 20 can accommodate both pace mapping and entrainment pacing techniques. The expanded structure 20 can also be used to convey pacing signals to confirm contact between tissue and the segments 44. The ability to carry out pacing to sense tissue contact is unexpected, given that the expanded structure 20 presents a surface area significantly greater than that presented by a conventional 4 mm/8F electrode.

Other types of expandable-collapsible electrode structures are well suited for pacing the heart as well.

Figure 9:
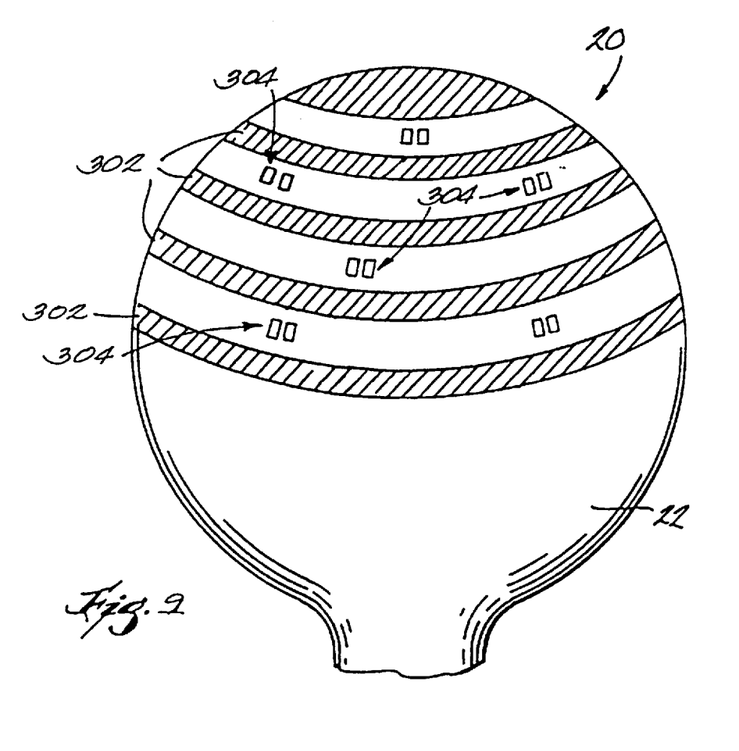
FIG. 9 is a side elevation view of an expandable-collapsible electrode structure with a bull's eye pattern of electrode zones.
Figure 10:
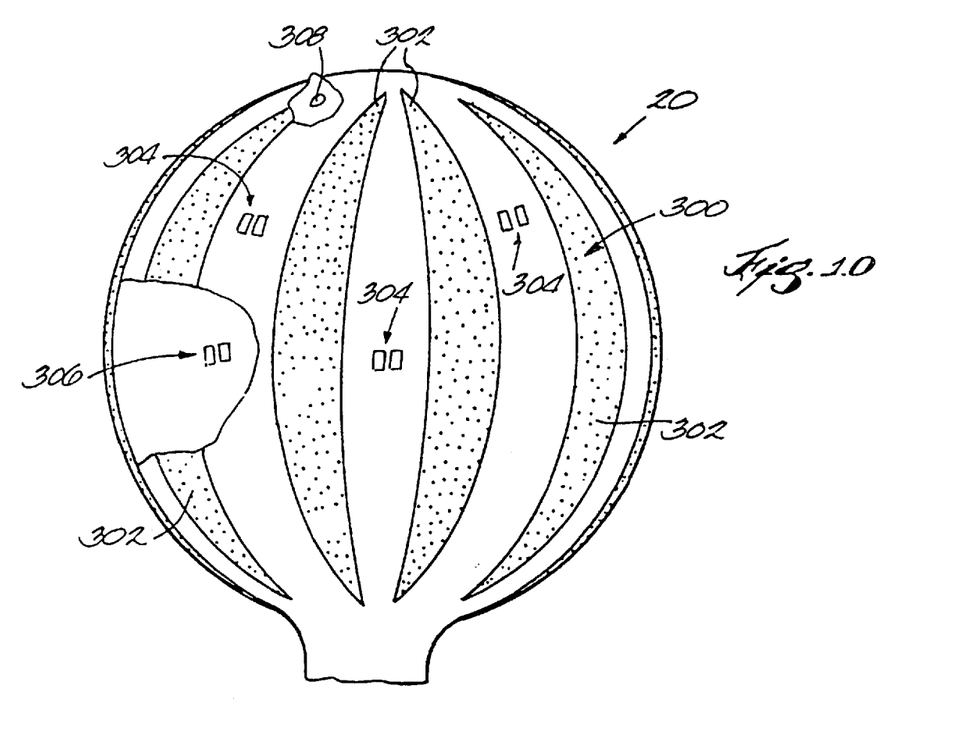
FIG. 10 an expandable-collapsible electrode structure with a circumferentially spaced pattern of electrode zones.

For example, FIG. 9 shows an expandable-collapsible body 22, as previously described, which carries an electrically conductive shell 300 that has been segmented into separate electrode zones 302 arranged in a concentric "bulls eye" pattern about the distal tip of the body 22. Alternatively, as FIG. 10 shows, the shell 300 can be segmented into axially elongated, circumferentially spaced electrode zones 302.

The electrode zones 302 are formed by masking regions on the body 22 which are to be free of the shell 300. A metal material having a relatively high electrical conductivity, as well as a relative high thermal conductivity, such as gold, platinum, platinum/iridium, among others, is deposited upon the unmasked regions on the body 22 by sputtering, vapor deposition, ion beam deposition, electroplating over a deposited seed layer, or a combination of these processes. Alternatively, preformed foil shells can be applied in axially spaced bands on the distal region to form the segmented zones. Still alternatively, the segmented zones can comprise signal wire snaked through the wall with noninsulated signal wire portions exposed on the exterior wall.

Regardless of the pattern, each zone 302 is coupled to a dedicated signal wire or a dedicated set of signal wires (not shown). In this arrangement, the controller 43 can direct ablation energy differently to each zone according to prescribed criteria. Furthermore, in this arrangement, a pacing signal can be conveyed to a selected one electrode zone. The electrode zones 302 can also serve to sense the resulting electrical events for the creation of electrograms.

In the illustrated and preferred embodiment (see FIGS. 9 and 10), smaller, bipolar electrode segments 304 are placed in the regions between the zones 304. These bipolar electrode segments 304, like the zones 302 themselves, comprise metal materials, such as gold, platinum, platinum/iridium, among others, deposited upon the body 22 by sputtering, vapor deposition, ion beam deposition, electroplating over a deposited seed layer, or a combination of these processes. Alternatively, preformed foil patches can be applied to form the bipolar segments. The bipolar segments 304 are electrically coupled to signal wires (not shown) to allow bipolar electrogram acquisition, pacing, or E-Characteristic measurements.

As FIG. 10 shows, the interior surface of the body 22 can also carry electrodes 306 suitable for unipolar or bipolar sensing or pacing or sensing of E-Characteristics. Different electrode placements can be used for unipolar or bipolar sensing or pacing. For example, pairs of 2-mm length and 1-mm width electrodes 306 can be deposited on the interior surface of the body 22. Connection wires (not shown) can be attached to these electrodes 306. Preferably the interelectrode distance is about 1 mm to insure good quality bipolar electrograms. Preferred placements of these interior electrodes 306 are at the distal tip and center of the structure 22. Also, when multiple zones 302 are used, it is desired to have the electrodes 306 placed in between the zones 302.

As FIG. 10 also shows, it is preferred to deposit opaque markers 308 on the interior surface of the body 22 so that the physician can guide the device under fluoroscopy to the targeted site. Any high-atomic weight material is suitable for this purpose. For example, platinum, platinum-iridium. can be used to build the markers 106. Preferred placements of these markers 308 are at the distal tip and center of the structure 22.

Figure 11:
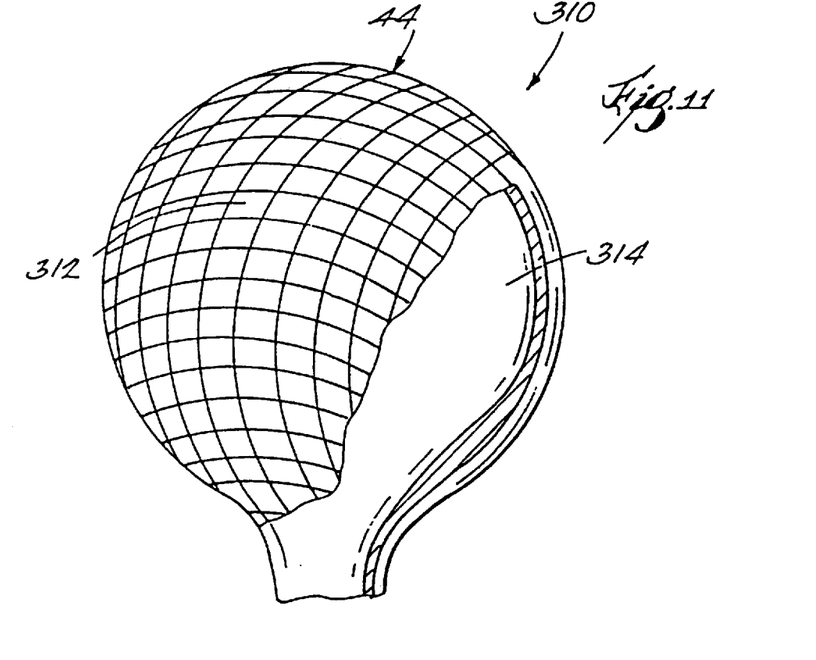
FIG. 11 is an expandable-collapsible electrode structure suitable for noncontact mapping of the interior of the heart.

FIG. 11 shows a structure 310 for mapping electrical activity within the heart without physical contact between the structure and endocardial tissue. The structure 310 comprises an expandable-collapsible body that takes the form of a mesh 312 made from interwoven resilient, inert wire or plastic filaments preformed to the desired expanded geometry. A sliding sheath (as previously shown and described in conjunction with FIG. 6) advanced along the catheter tube 12 compresses the mesh structure 312 to collapse it. Likewise, retraction of the sheath removes the compression force, and the freed mesh structure 312 springs open.

By interweaving the mesh filaments close enough together, the mesh structure 312 serves as the support for the electrode segments 44, which can be deposited on the filaments as on a shell supported by the filaments. Alternatively, all or a portion of the mesh filaments could be made electrically conductive. The network of the filaments makes it possible to form electrodes whose spacial location can be determined.

Alternatively, as FIG. 11 also shows, the mesh structure 312 can be made to normally assume the collapsed geometry. In this arrangement, one or more interior bladders 314 can accommodate the introduction of an inflation medium to cause the mesh structure 312 to assume the expanded geometry.

If the mesh structure 312 is tightly woven enough to be essentially liquid impermeable, the interior bladder could be eliminated. In this arrangement, the introduction of a biocompatible liquid, such as sterile saline, directly into the interior of the structure 312 would cause the structure to assume the expanded geometry.

The expandable-collapsible mesh structure 312 can be positioned within the blood pool of a heart chamber. The electrode segments 44 sense electrical potentials in blood. Electrical potentials in myocardial tissue can be inferred from the sensed blood potentials, without actual contact with the endocardium. Further details of this methodology are found in Pilkington, Loftis, Thompson et al.(Ed.), *High Performance Computina in Biomedical Research* (Part 3), "Inverse Problems and Computational Methods," CRC Press, Inc. (1993), and Jackman, Beatty, Scherlag et al., "New Noncontact Catheter Multiple Electrode Array Accurately Reconstructs Left Ventricular Endocardial Potentials," *Pace,* v.18, N.4(2), p. 898 (1995).

It should be appreciated that expandable-collapsible bodies carrying deposited electrically conductive shells or electrode segments, as previously discussed and shown in FIGS. 2 to 10, could also be used for noncontact mapping in the manner just described.

Further details of the structure of various expandable-collapsible electrode bodies and how to assemble them are described in copending patent application entitled "Expandable-Collapsible Electrode Structures" filed concurrently with this application.

Various features of the invention are set forth in the following claims.

We claim:

1. A system for using in association with body tissue comprising a structure including an exterior wall adapted to contact tissue, the exterior wall adapted to selectively assume an expanded geometry having a first maximum diameter and a collapsed geometry having a second maximum diameter less than the first maximum diameter, an array of electrically conducting electrode segments carried by the exterior wall of the structure, an electrically conductive network coupled to the electrode segments, including at least one electrically conductive path individually coupled to each electrode segment, and a controller coupled to the electrically conductive network, the controller operating in a first mode during which the network is electrically conditioned to individually sense at each electrode segment local electrical events in tissue, the controller further operating in a second mode during which the network is electrically conditioned, based at least in part upon local electrical events sensed by the electrode segments, to couple at least two electrode segments together to simultaneously transmit electrical energy to create a physiological effect upon a region of body tissue.

2. A system according to claim 1
wherein, in the first mode, the controller electrically conditions the network to sense local electrical potentials in body tissue with individual electrode segments.

3. A system according to claim 1
wherein, in the first mode, the controller electrically conditions the network to sense local resistivity in body tissue with individual electrode segments.

4. A system according to claim 1
wherein, in the first mode, the controller electrically conditions the network to sense local impedance in body tissue with individual electrode segments.

5. A system according to claim 1
and further including at least one temperature sensing element carried by the exterior wall in association with the array of electrically conducting electrode segments.

6. A system for use in association with body tissue comprising
a structure including an exterior wall adapted to contact tissue,
an array of electrically conducting electrode segments carried by the exterior wall of the structure,
an electrically conductive network coupled to the electrode segments, including at least one electrically conductive path individually coupled to each electrode segment, and
a controller coupled to the electrically conductive network, the controller operating in a first mode during which the network is electrically conditioned to individually transmit through each electrode segment electrical energy creating a local physiological effect upon body tissue, the controller further operating in a second mode during which the network is electrically conditioned to couple at least two electrode segments together to simultaneously transmit electrical energy creating a regional physiological effect upon body tissue.

7. A system according to claim 6
wherein, in the first mode, the controller electrically conditions the network to locally stimulate body tissue with electrical energy individually transmitted by the electrode segments.

8. A system according to claim 6
wherein the controller further operates in a third mode during which the network is electrically conditioned to individually sense at each electrode segment local electrical events in tissue.

9. A system according to claim 8
wherein, in the third mode, the controller electrically conditions the network to sense local electrical potentials in heart tissue with individual electrode segments.

10. A system according to claim 8
wherein, in the third mode, the controller electrically conditions the network to sense local resistivity in heart tissue with individual electrode segments.

11. A system according to claim 8
wherein, in the third mode, the controller electrically conditions the network to sense local impedance in heart tissue with individual electrode segments.

12. A system according to claim 1 or 6
wherein, in the second mode, the controller electrically conditions the network to heat a region of body tissue with electrical energy simultaneously transmitted by at least two electrode segments.

13. A system according to claim 1 or 6
wherein, in the second mode, the controller electrically conditions the network to ablate a region of body tissue with electrical energy simultaneously transmitted by at least two electrode segments.

14. A system according to claim 6 and further including at least one temperature sensing element carried by the exterior wall in association with the array of electrically conducting electrode segments.

15. A system for ablating heart tissue comprising
a structure including an exterior wall adapted to contact heart tissue, the exterior wall adapted to selectively assume an expanded geometry having a first maximum diameter and a collapsed geometry having a second maximum diameter less than the first maximum diameter,
an array of electrically conducting electrode segments carried by the exterior wall of the structure,
an electrically conductive network coupled to the electrode segments, including at least one electrically conductive path individually coupled to each electrode segment, and
a controller coupled to the electrically conductive network, the controller operating in a first mode during which the network is electrically conditioned to individually sense at each electrode segment a local electrical event in heart tissue, the controller further operating in a second mode during which the network is electrically conditioned, based at least in part upon local electrical events individually sensed by the electrode segments, to couple at least two electrode segments together to simultaneously transmit radio frequency electrical energy to ablate a region of heart tissue.

16. A system according to claim 15
wherein, in the first mode, the controller electrically conditions the network to sense local electrical potentials in heart tissue with individual electrode segments.

17. A system according to claim 15
wherein, in the first mode, the controller electrically conditions the network to sense local resistivity in heart tissue with individual electrode segments.

18. A system according to claim 15
wherein, in the first mode, the controller electrically conditions the network to sense local impedance in heart tissue with individual electrode segments.

19. A system according to claim 15
and further including at least one temperature sensing element carried by the exterior wall in association with the array of electrically conducting electrode segments.

20. A system for ablating heart tissue comprising
a structure including an exterior wall adapted to contact heart tissue,
an array of electrically conducting electrode segments carried by the exterior wall of the structure,
an electrically conductive network coupled to the electrode segments, including at least one electrically conductive path individually coupled to each electrode segment, and a controller coupled to the electrically conductive network, the controller operating in a first mode during which the network is electrically conditioned to individually transmit through each electrode segment electrical energy to pace heart tissue, the controller further operating in a second mode during which the network is electrically conditioned to couple at least two electrode segments together to concurrently transmit radio frequency electrical energy to ablate a region of heart tissue.

21. A system according to claim 20
wherein the controller further operates in a third mode during which the network is electrically conditioned to individually sense at each electrode segment local electrical events in heart tissue.

22. A system according to claim 21
wherein, in the third mode, the controller electrically conditions the network to sense local electrical potentials in heart tissue with individual electrode segments.

23. A system according to claim 21
wherein, in the third mode, the controller electrically conditions the network to sense local resistivity in body tissue with individual electrode segments.

24. A system according to claim 21
wherein, in the third mode, the controller electrically conditions the network to sense local impedance in body tissue with individual electrode segments.

25. A system according to claim 20
and further including at least one temperature sensing element carried by the exterior wall in association with the array of electrically conducting electrode segments.

26. A system according to claim 1 or 6 or 15 or 20
wherein the exterior wall peripherally surrounds an interior area,
and further including a lumen to convey a medium containing ions into the interior area,
and wherein at least a portion of the exterior wall comprises a porous material sized to pass ions contained in the medium.

27. A system according to claim 26
wherein the porous material comprises an ultrafiltration membrane.

28. A system according to claim 26
wherein the porous material comprises a microporous membrane.

29. A system according to claim 26
and further including an electrically conductive element contacting the medium within the interior area to transmit electrical energy for ionic transport through the medium and porous material.

30. A system according to claim 26
wherein the porous wall has an electrical resistivity of equal to or greater than about 500 ohm·cm.

31. A system according to claim 26
wherein the porous wall has an electrical resistivity of less than about 500 ohm·cm.

32. A system according to claim 1 or 6 or 15 or 20
wherein the exterior wall is electrically conductive and peripherally surrounds an interior area, and
further including a lumen to convey a medium containing ions into the interior area, and an electrically conductive element contacting the medium within the interior area to transmit electrical energy for ionic transport through the medium.

33. A system according to claim 32
wherein the exterior wall has an electrical resistivity of equal to or greater than about 500 ohm·cm.

34. A system according to claim 32
wherein the exterior wall has an electrical resistivity of less than about 500 ohm·cm.

35. A system according to claim 32
and wherein at least a portion of the exterior wall comprises a porous material sized to pass ions contained in the medium.

36. A system according to claim 35
wherein the porous material has an electrical resistivity of equal to or greater than about 500 ohm·cm.

37. A system according to claim 35
wherein the porous material has an electrical resistivity of less than about 500 ohm·cm.

38. A system according to claim 35
wherein the porous material comprises an ultrafiltration membrane.

39. A system according to claim 35
wherein the porous material comprises a microporous membrane.

40. A system according to claim 6 or 20
wherein the exterior wall is adapted to selectively assume an expanded geometry having a first maximum diameter and a collapsed geometry having a second maximum diameter less than the first maximum diameter.

41. A system according to claim 1 or 6 or 15 or 20
wherein the exterior wall peripherally surrounds an interior area,
and further including a support structure underlying the wall.

42. A system according to claim 41
wherein the support structure is adapted to selectively assume an expanded geometry having a first maximum diameter and a collapsed geometry having a second maximum diameter less than the first maximum diameter.

43. A system according to claim 1 or 6 or 15 or 20
wherein the electrode segments comprise a coating deposited on the exterior wall.

44. A system according to claim 1 or 6 or 15 or 20
wherein the electrode segments comprise foil affixed to the exterior wall.

45. A system according to claim 1 or 6 or 15 or 20
wherein the electrically conductive electrode segments comprise noninsulated signal wire exposed on the exterior wall.

46. A system for using in association with body tissue comprising
a structure including an exterior wall adapted to contact tissue, the exterior wall including a distal region and a proximal region,
an array of electrically conducting electrode segments carried by the exterior wall of the structure, the array of electrically conducting electrode segments occupying more of the distal region than the proximal region.
an electrically conductive network coupled to the electrode segments, including at least one electricaly conductive path individually coupled to each electrode segment, and
a controller coupled to the electrically conductive network, the controller operating in a first mode during which the network is electrically conditioned to individually sense at each electrode segment local electrical events in tissue, the controller further operating in a second mode during which the network is electrically conditioned, based at least in part upon local electrical events sensed by the electrode segments, to couple at least two electrode segments together to simultaneously transmit electrical energy to create a physiological effect upon a region of body tissue.

47. A system according to claim 46
wherein at least 1/3rd of the proximal region is free of the array of electrically conducting electrode segments.

48. A system according to claim 46
wherein the array of electrically conducting electrode segments occupies at least 1/3rd of the distal region.

49. A system according to claim 1 or 6 or 15 or 20
wherein the array of electrically conducting electrode segments is arranged in radially spaced zones.

50. A system according to claim 1 or 6 or 15 or 20
wherein the array of electrically conducting electrode segments is arranged in circumferentially spaced zones.

51. A system for pacing heart tissue comprising
a structure including an exterior wall adapted to contact heart tissue, the exterior wall adapted to selectively assume an expanded geometry having a first maximum diameter and a collapsed geometry having a second maximum diameter less than the first maximum diameter,
electrically conducting electrodes on the exterior wall of the structure,
an electrically conductive network coupled to the electrodes, including at least one electrically conductive path individually coupled to each electrode, and
a controller coupled to the electrically conductive network, the controller operating in a first mode during which the network is electrically conditioned to transmit electrical energy through the electrodes to pace heart tissue, the controller further operating in a second mode during which the network is electrically conditioned to sense electrical events through the electrodes.

52. A system according to claim 51
wherein, in the first mode, the network is electrically conditioned to carry out pacing mapping.

53. A system according to claim 51
wherein, in the first mode, the network is electrically conditioned to carry out entrainment pacing.

54. A system according to claim 51
wherein the controller further operates in a third mode during which the network is electrically conditioned to transmit radio frequency electrical energy through at least two of the electrodes to ablate heart tissue.

55. A system according to claim 51
wherein the exterior wall includes a distal region and a proximal region, and
wherein the electrodes occupy more of the distal region than the proximal region.

56. A system according to claim 51
wherein at least 1/3rd of the proximal region is free of the electrodes.

57. A system according to claim 51
wherein the electrodes occupy at least 1/3rd of the distal region.

58. A system according to claim 51
wherein the electrodes are arranged in radially spaced segments.

59. A system according to claim 51
wherein the electrodes are arranged in circumferentially spaced segments.

60. A system according to claim 51
wherein the electrodes comprise a coating deposited on the exterior wall.

61. A system according to claim 51
wherein the electrodes comprise foil affixed to the exterior wall.

62. A system according to claim 51
wherein the electrodes comprise noninsulated signal wire exposed on the exterior wall.

63. A system according to claim 51
and further including at least one temperature sensing element carried by the exterior wall in association with the array of electrically conducting electrodes.

64. A method for heating body tissue comprising the steps of
placing a structure having an exterior wall in contact with body tissue, the exterior wall adapted to selectively assume an expanded geometry having a first maximum diameter and a collapsed geometry having a second maximum diameter less than the first maximum diameter, the structure including an array of electrically conducting electrode segments carried by the exterior wall and an electrically conductive network coupled to the electrode segments, including at least one electrically conductive path individually coupled to each electrode segment,
operating in a first mode during which the network is electrically conditioned to individually sense at each electrode segment local electrical events in tissue, and
operating in a second mode during which the network is electrically conditioned, based at least in part upon local electrical events sensed by the electrode segments, to couple at least two electrode segments together to simultaneously transmit electrical energy to heat a region of body tissue.

65. A method according to claim 64
wherein, when operating in the first mode, the network senses local electrical potentials in body tissue with individual electrode segments.

66. A method according to claim 64
wherein, when operating in the first mode, the network senses local resistivity in body tissue with individual electrode segments.

67. A method according to claim 64
wherein, when operating in the first mode, the network senses local impedance in body tissue with individual electrode segments.

68. A method according to claim 64
and further including the step of operating in a third mode, during which the network is electrically conditioned to individually transmit through each electrode segment electrical energy to locally stimulate body tissue.

69. A method according to claim 64
wherein, when operating in the second mode, the network ablates body tissue.

70. A method according to claim 64
wherein, in placing a structure, the exterior wall is placed in contact with heart tissue.

71. A method according to claim 64
and further including the step, while operating in the second mode, of sensing temperature.

72. A method for pacing heart tissue comprising the steps of provicing a structure including an exterior wall adapted to selectively assume an expanded geometry having a first maximum diameter and a collapsed geometry having a second maximum diameter less than the first maximum diameter, the structure including electrically conducting electrodes on the exterior wall of the structure and an electrically conductive network coupled to the electrodes, including at least one electrically conductive path individually coupled to each electrode, and guiding the structure into a heart chamber while in the collapsed geometry, causing the structure to assume the expanded geometry within the heart chamber, placing the structure, when in the expanded geometry, in contact with heart tissue within the heart chamber, operating in a first mode during which the network is electrically conditioned to transmit electrical energy through the electrodes to pace heart tissue, and operating in a second mode during which the network is electrically conditioned to sense electrical events through the electrodes.

73. A method according to claim 72 wherein, in the first mode, the network is electrically conditioned to carry out pacing mapping.

74. A method according to claim 72 wherein, in the first mode, the network is electrically conditioned to carry out entrainment pacing.

75. A method according to claim 72 and further including the step of operating in a third mode during which the network is electrically conditioned to transmit radio frequency electrical energy through at least two of the electrodes to ablate heart tissue.

76. A method according to claim 75 and further including the step, while operating in the third mode, of sensing temperature.

77. A system for diagnosing and treating body tissue, comprising:

a structure including a wall, the wall including an exterior adapted to contact tissue;

an array of electrically conducting electrode segments carried by the exterior of the wall of the structure and arranged in spaced apart zones, the spaced apart zones defining a region of the wall between the zones;

an electrically conductive network coupled to the electrode segments, including at least one electrically conductive path individually coupled to each electrode segment;

a controller coupled to the electrically conductive network, the controller operating in a first mode during which the network is electrically configured to individually sense at each electrode segment local electrical activity in the body tissue, the controller further operating in a second mode during which the network is electrically configured, based at least in part upon local electrical events sensed by the electrode segments, to couple at least two electrode segments together to simultaneously transmit electrical energy to create a physiological effect upon a region of body tissue, and additional electrode segments carried by the region of the wall between the zones and coupled to the controller.

78. A system according to claim 77, wherein the additional electrode segments are carried by the exterior of the wall.

79. A system according to claim 78, wherein the additional electrode segments include bipolar electrode segments adapted to allow a function selected from the group consisting of acquiring bipolar electrograms, pacing, and acquiring E-Characteristic measurements.

80. A system according to claim 78, wherein the additional electrode segments are smaller than the electrode segments of the array.

81. A system according to claim 77, and wherein the wall includes an interior, and wherein the additional electrode segments are carried by the interior of the wall.

82. A system according to claim 81, wherein the additional electrode segments are adapted to allow a function selected from the group consisting of unipolar sensing, bipolar sensing, pacing, and acquiring E-Characteristic measurements.

83. A system according to claim 81, wherein the interelectrode distance is approximately 1 mm.

84. A system according to claim 81, wherein the structure includes a distal tip, a proximal tip, and a center located between the distal tip and proximal tip, and wherein the electrode segments are carried at a location on the structure selected from the group consisting of the distal tip and the center.

* * * * *